United States Patent

Yamamori et al.

[11] Patent Number: 5,728,585
[45] Date of Patent: Mar. 17, 1998

[54] CAPNOMETER

[75] Inventors: Shinji Yamamori; Hidehiro Hosaka; Kohei Ono; Masami Ito; Masayuki Inoue; Masaki Sugiura, all of Tokyo, Japan

[73] Assignee: Nihon Kohden Corporation, Tokyo, Japan

[21] Appl. No.: 605,845

[22] Filed: Feb. 26, 1996

[30] Foreign Application Priority Data

| Feb. 24, 1995 | [JP] | Japan | 7-037239 |
| Feb. 24, 1995 | [JP] | Japan | 7-037361 |
| Feb. 24, 1995 | [JP] | Japan | 7-037411 |

[51] Int. Cl.[6] .................................................. G01N 33/497
[52] U.S. Cl. ........................................ 436/133; 422/84
[58] Field of Search ....................... 422/83–84; 436/133, 436/134

[56] References Cited

U.S. PATENT DOCUMENTS

| 4,067,320 | 1/1978 | Olsson et al. | 128/2 C |
| 4,648,396 | 3/1987 | Raemer | 128/204.22 |
| 4,653,498 | 3/1987 | New, Jr. et al. | 128/633 |
| 5,281,817 | 1/1994 | Yelderman et al. | 250/343 |
| 5,401,966 | 3/1995 | Gray et al. | 250/343 |

FOREIGN PATENT DOCUMENTS

| 51-136474 | 11/1976 | Japan . |
| 53-53184 | 5/1978 | Japan . |
| 59-160446 | 9/1984 | Japan . |

*Primary Examiner*—Lyle A. Alexander
*Attorney, Agent, or Firm*—Sughrue, Mion, Zinn, Macpeak & Seas, PLLC

[57] ABSTRACT

A capnometer is disclosed with a light sourse for irradiating a respirtory gas, a thermal detector for sensing the transmission of the infrared radiation, a switch device for turning the radiation source on and off in a predetermined period, a memory device for storing output from the thermal deterctor, and a control device for picking up a maximum value of the detection signal from the thermal detector for the present inspiration phase. The maximum value is stored in the memory device and the difference is calculated between a subsequently issued detection signal and the stored maximum value to compensate for drift that has occurred in the thermal detector.

12 Claims, 7 Drawing Sheets

CAPNOMETER

BACKGROUND OF THE INVENTION

Field of Invention

The present invention relates to a capnometer for measuring the concentration of carbon dioxide in expired gases.

Field of the Invention

Infrared measurements of carbon dioxide in expired gases are commonly performed with radiation detectors that sense the transmission of radiation associated with the adsorption by the carbon dioxide during expiration. The output voltage of the detector is subject to drift for various reasons including the variation in the intensity of radiation from the source and the change in the quantity of radiation due to the contamination of the windows in the sensing part. An apparatus adapted to compensate for such drift is known in the art (see Examined Japanese Patent Publication No. 44614/1985).

FIG. 9 shows diagrammatically the construction of a capnometer equipped with the known drift compensator. Shown by 40 in FIG. 9 is a tube through which a respiratory gas will pass. One end of the tube 40 is a mouthpiece which is to be inserted into the mouth of a patient and the other end of the hose branches into two parts, one being open to the atmosphere and the other being connected to a servo blower 41 which supplies the patient with air during the inspiration phase. A pair of light-transmitting windows 41a and 41b typically made of sapphire are formed in the middle portion of the hose 40. A radiation source 42 is provided below the window 41b and a radiation interrupter 43 that has a light-transmitting aperture and which is typically driven to rotate by means of a motor M is provided above the window 41a. Located above the radiation interrupter 43 is a filter 44 that passes only those rays which are absorbed by carbon dioxide and a radiation detector 45 is located above the filter 44. Shown by 46 is an amplifier for amplifying the output voltage of the detector 45; 47 is a rectifier; 48 is a divider; 49 is a logarithmic amplifier; 50 is a recording device; 51 is a field-effect transistor (FET) that conducts during the inspiration period in response to the output of servo blower 41; and 52 is a memory that holds a voltage corresponding to $CO_2$ concentration of zero during the inspiration period and which delivers it as an output to the divider 48.

With this arrangement, the radiation from the source 42 passes through the window 41a and the respiratory gas in the hose 40 and emerges from the window 41b to enter the radiation interrupter 43, which chops the incident light at periodic intervals. The chopped rays of light pass through the filter 44 and the transmission of radiation associated with the $CO_2$ concentration is sensed by the detector 45. The output signal from the detector 45 is given as an expotential function, amplified by the amplifier 46 and rectified by the rectifier 47.

The output from the radiation detector 45 contains a drift due, for example, to the change in the quantity of radiation caused by contamination of the filter 44 and windows 41a and 41b and to the variation in the intensity of radiation from the source 42. In order to reject the drift component from the output voltage of the rectifier 47, the servo blower 41 delivers a positive signal to FET 51 during the inspiration period, whereby the FET conducts and a voltage corresponding to $CO_2$ concentration of zero is held in the memory 52, from which it is delivered as an output to the divider 48. Upon ending of the inspiration period, the positive signal from the servo blower 41 disappears and the FET 51 turns off and the output of the rectifier 47 (i.e., a signal associated with the $CO_2$ concentration in the expired gas) is delivered to the divider 48 and divided by the voltage held in the memory 52 which corresponds to $CO_2$ concentration of zero, whereby the drift component is eliminated. The output of the divider 48 is delivered to the logarithmic amplifier 49 to produce an output signal proportional to the $CO_2$ concentration of the expired gas.

A problem with this capnometer equipped with the prior art drift compensator in a radiation detector is that the detector uses the rather expensive PbSe. This material features fast response but the device temperature will increase upon continued exposure to an infrared radiation and the decreasing resistance will increase the drift. To avoid this problem, the radiation from the source has to be repeatedly chopped at a frequency, say, 200 Hz, higher than the respiration frequency. To meet this need, a radiation interrupter and a drive mechanism such as a motor that drives its rotation have been used to detect the quantity of radiation passing through the respiratory gas. However, this has limited the efforts to reduce the overall size of the system and its power consumption while assuring ruggedness. In addition, the prior art system has had the disadvantage of being costly.

SUMMARY OF THE INVENTION

The present invention has been accomplished under these circumstances and has as an object providing a capnometer that is capable of compensation for a sensitivity drift of the detector included in the detecting signal and a sensitivity drift, such as an amplitude variation, occurred by changing a light intensity of the light source or changing the quantity of radiation caused by contamination of the filter or the like, such as amplitude variation without employing any mechanism for cyclically chopping the infrared light necessary for the Pbse radiation detector.

This object of the invention can be attained by the capnometer which operates on the principle of applying an infrared radiation to a respiratory gas and detecting a signal associated with the quantity of transmitted radiation for measuring the concentration of carbon dioxide in the respiratory gas and which is characterized by comprising:

a thermal detector for sensing the transmission of said infrared radiation; switch means for turning the radiation source on and off; memory means; and control means picking up a maximum value of the detection signal from said thermal detector for the present inspiration phase, storing the maximum value in said memory means and calculating the difference between a subsequently issued detection signal and the stored maximum value, compensating a drift occurred on the basis of the thermal detector characteristic to determine a varying density signal, picking up a minimum output value, corresponding to an offset value, of the detection signal from said thermal detector when said radiation source is turned off momentarily, calculating the difference between said minimum value and the stored maximum value for the present inspiration phase, storing the calculated difference in said memory means as a reference value corresponding to carbon dioxide concentration of zero and with a maximum reception of infrared radiation at that time, storing said reference value in said memory means, calculating the ratio of said density signal to said reference value, and determining the concentration of carbon dioxide through compensation of a sensitivity corresponding to an amplitude.

In the capnometer of the present invention, the radiation source is turned off at a specified cycle longer than the cycle of respiration.

In the capnometer of the present invention, the radiation source is turned off in synchronism with the inspiration.

In the capnometer of the present invention, the radiation source is turned off when the difference between the maximum values picked up in adjacent inspiration phases exceeds a specified value.

Operation:

In the capnometer of the present invention, the quantity of infrared radiation from the source that has passed through the respiratory gas is sensed by the thermal detector and a maximum value of the detection signal from said thermal detector is picked up for each successive inspiration phase and stored in the memory means. The difference between a subsequently issued detection signal and the stored maximum value is calculated to determine a varying density signal and there is subjected the compensation of a drift occurred by the thermal defecter characteristic. Then, the radiation source is turned off momentarily and a minimum value, corresponding to the offset, of the resulting detection signal from the thermal detector is picked up and the difference from the stored maximum value is calculated to determine a reference value corresponding to carbon dioxide concentration of zero and with a maximum reception of infrared radiation at that time. The thus determined reference value is stored in the memory means. Thereafter, that ratio of the density signal to the reference value is calculated and used to correct the sensitivity of the density signal to determine a density signal which, in turn, is used to determine the correct $CO_2$ concentration.

In the capnometer of the present invention, the radiation source is turned off at a longer cycle than a predetermined cycle of respiration.

In the capnometer of the present invention, the radiation source is turned off in synchronism with the inspiration.

In the capnometer of the present invetion, the radiation source is turned off when the difference between the maximum values picked up in adjacent inspiration phases exceeds a predetermined value.

DETAILED DESCRIPTION OF THE PREFERRED EMBODIMENTS

Figure 1:
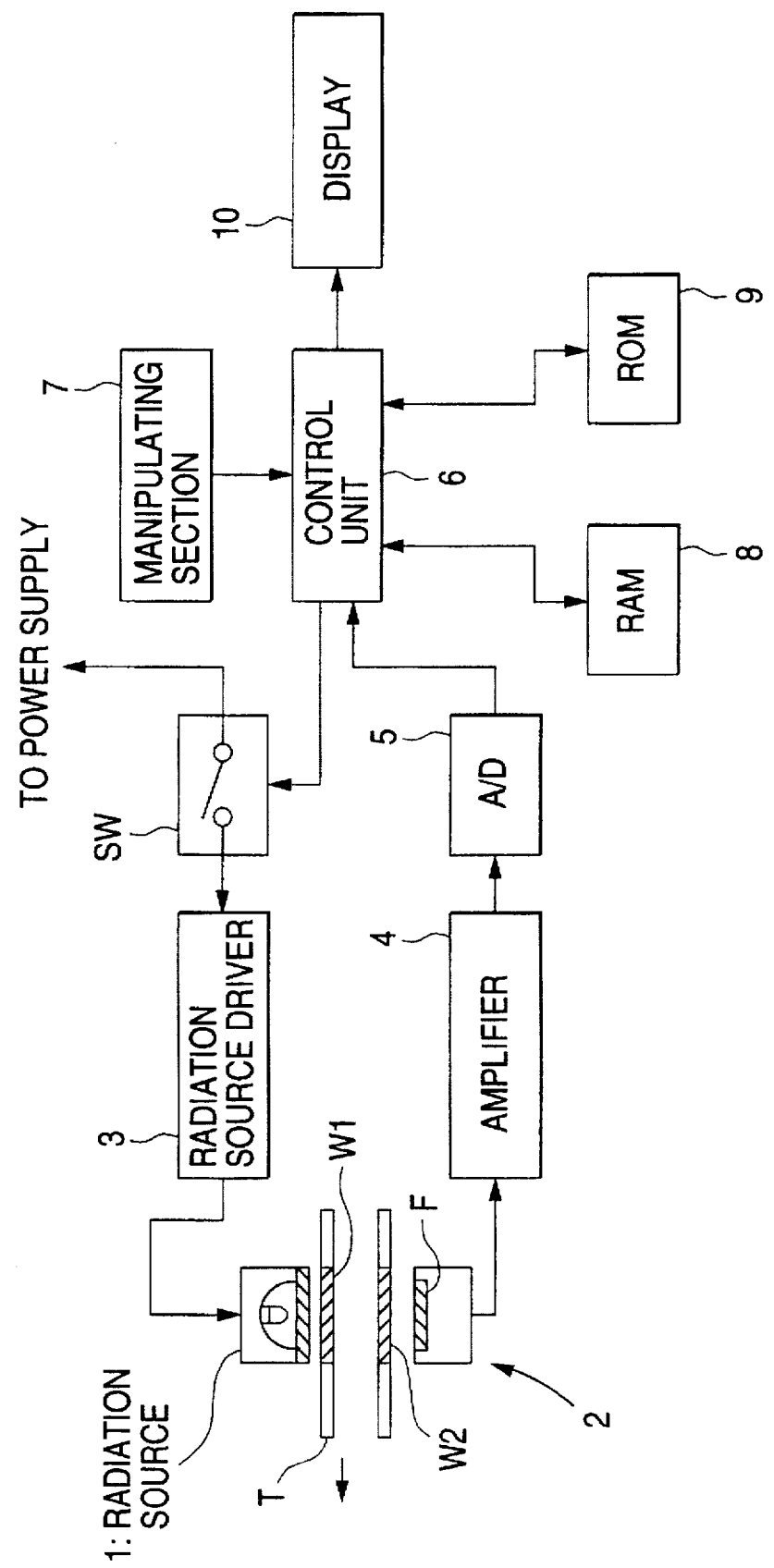
FIG. 1 is a block diagram showing the composition of the capnometer of the invention.
Figure 2:
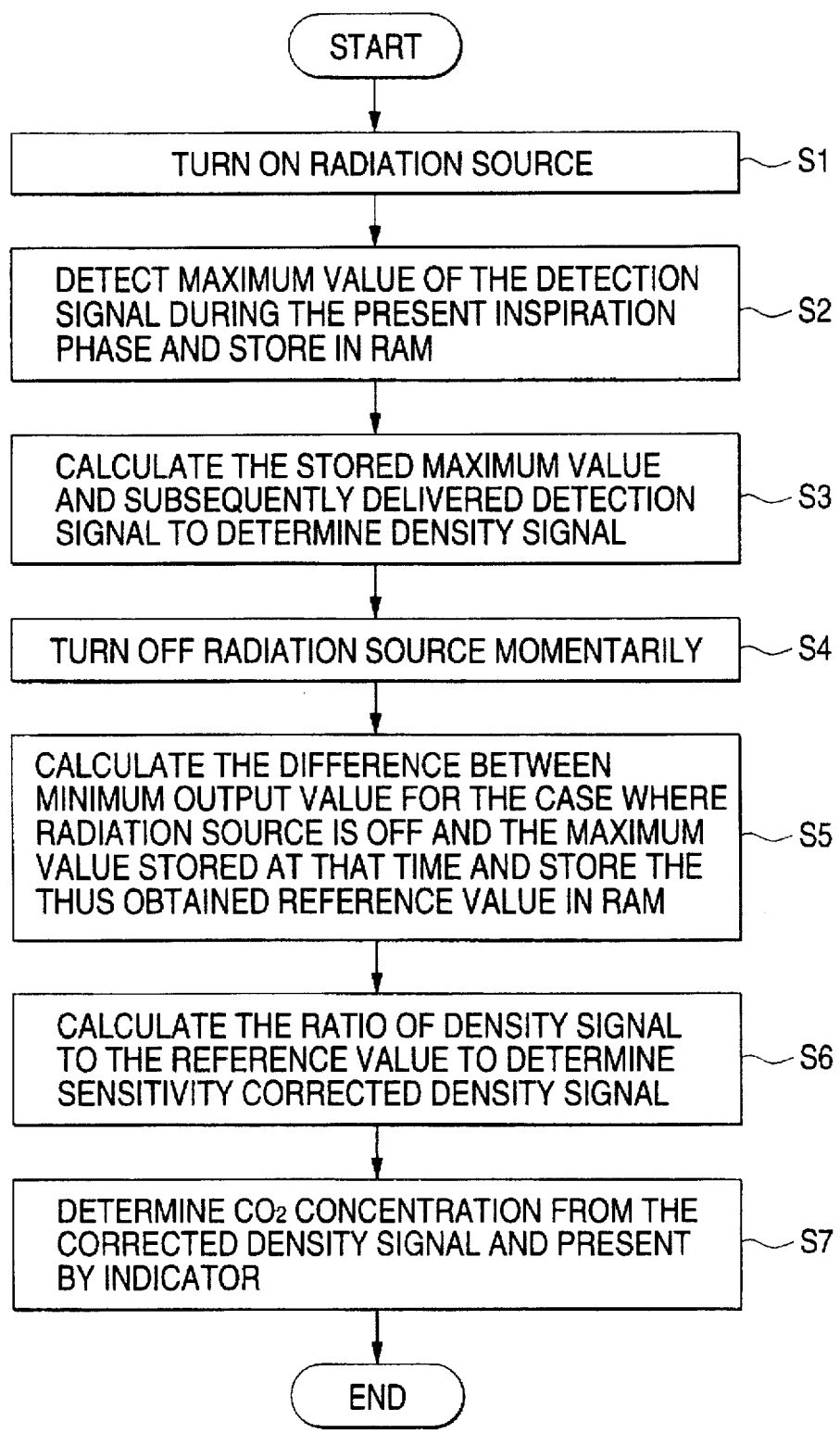
FIG. 2 is a flowchart describing the sequence of processing steps in the embodiment shown in FIG. 1.
Figure 3:
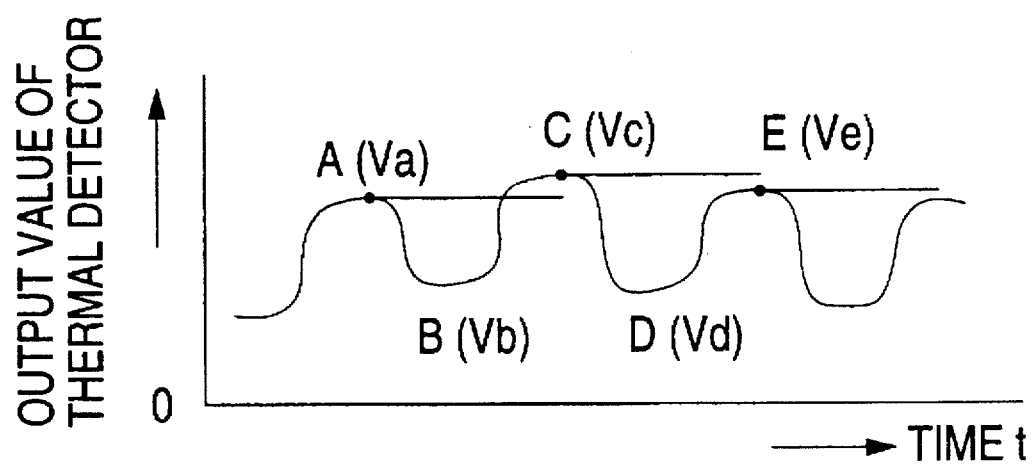
FIG. 3 illustrates the method of performing drift compensation in the embodiment shown in FIG. 1.
Figure 4:
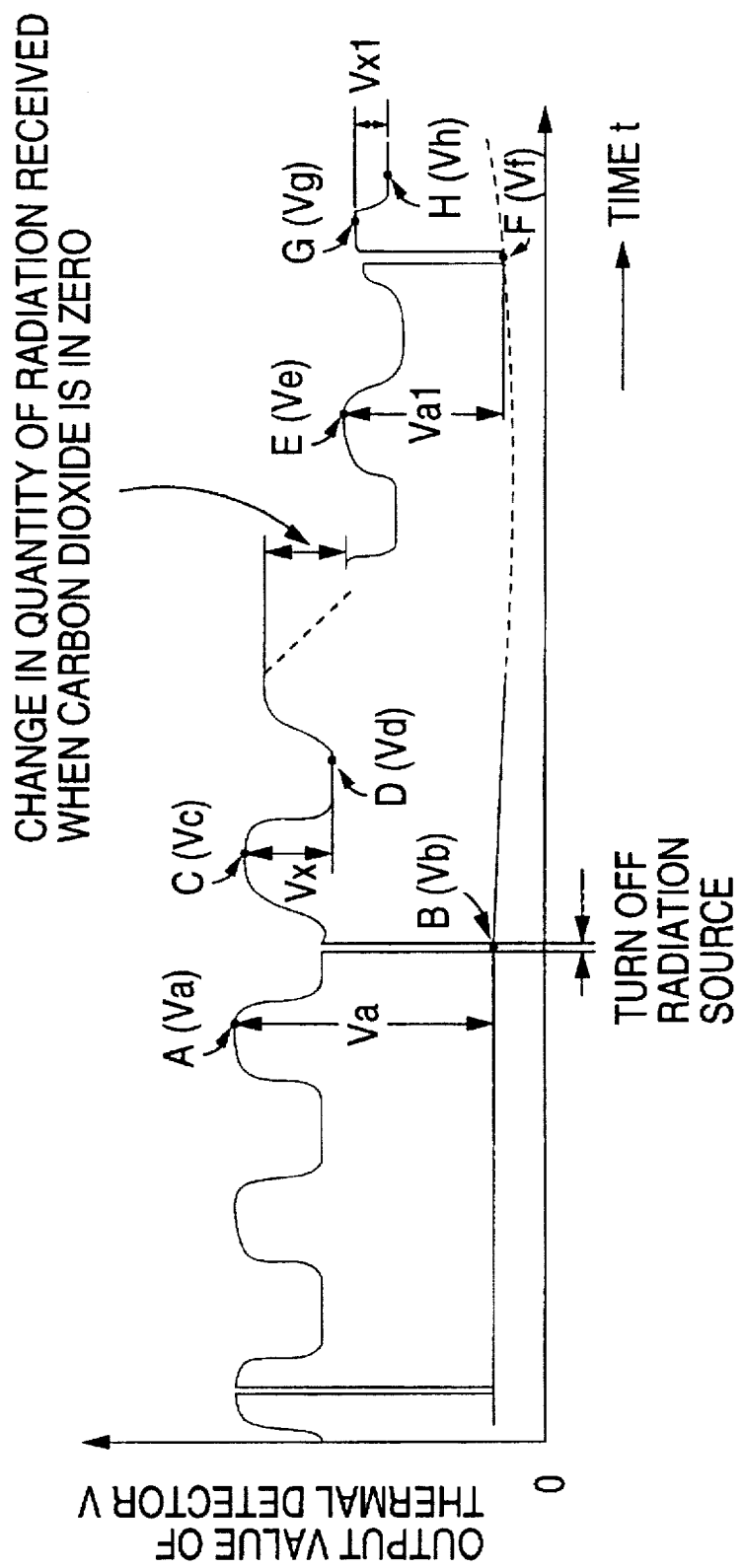
FIG. 4 illustrates the method of performing sensitivity correction in the embodiment shown in FIG. 1.
Figure 5:
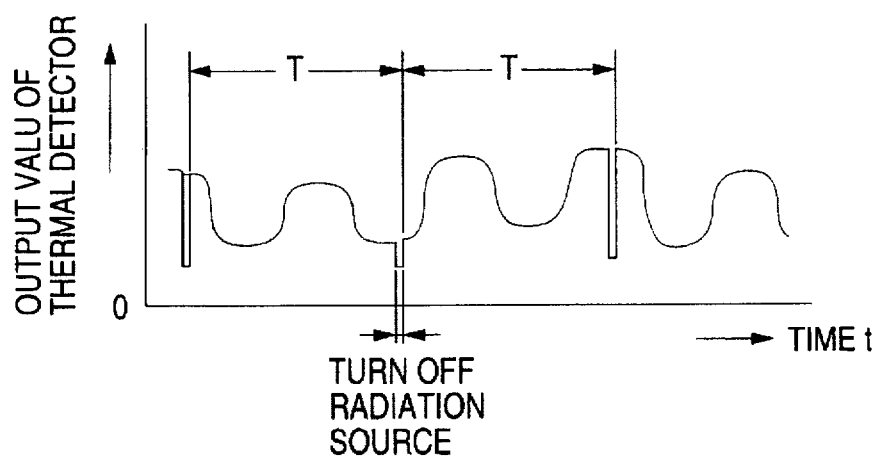
FIG. 5 is a timing chart for the case of turning off the radiation source at a specified period in the embodiment shown in FIG. 1.
Figure 6:
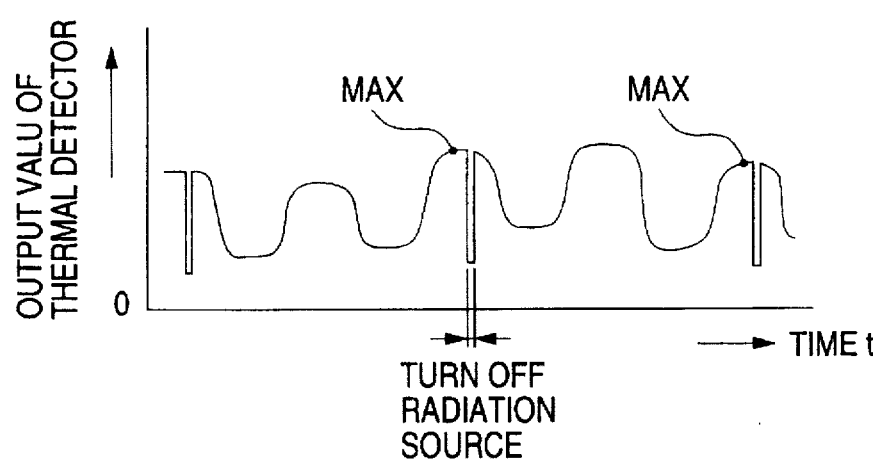
FIG. 6 is a timing chart for the case of turning off the radiation source in synchronism with the inspiration.
Figure 7:
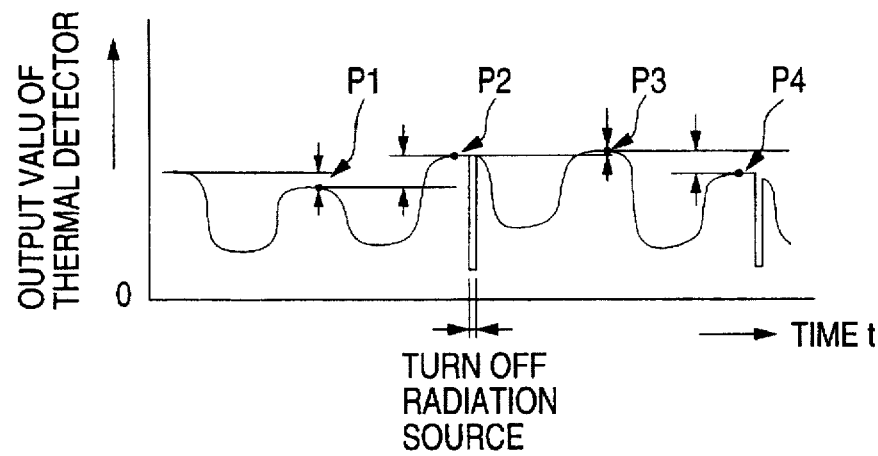
FIG. 7 is a timing chart for the case of turning off the radiation source when the difference between maximum values as picked up from the detection signal of the thermal detector during adjacent inspiration phases exceeds a specified value in the embodiment shown in FIG. 1.
Figure 8:
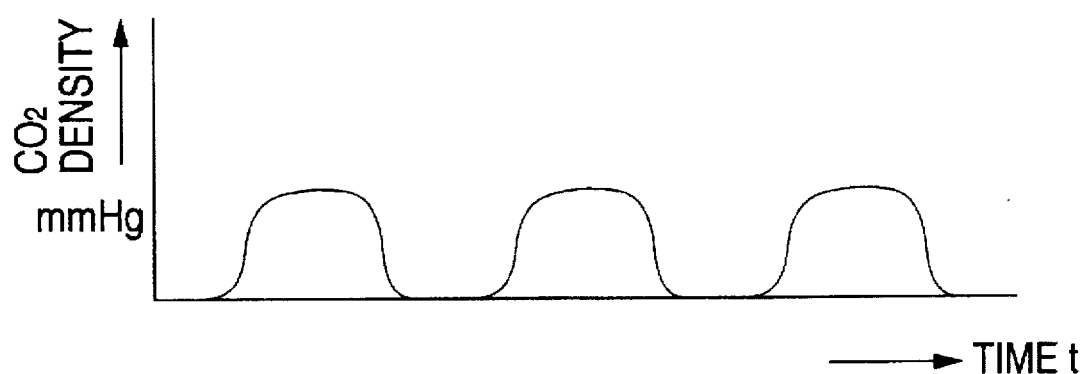
FIG. 8 is a timing chart showing the waveforms obtained by measuring the $CO_2$ concentration in the embodiment shown in FIG. 1.
Figure 9:
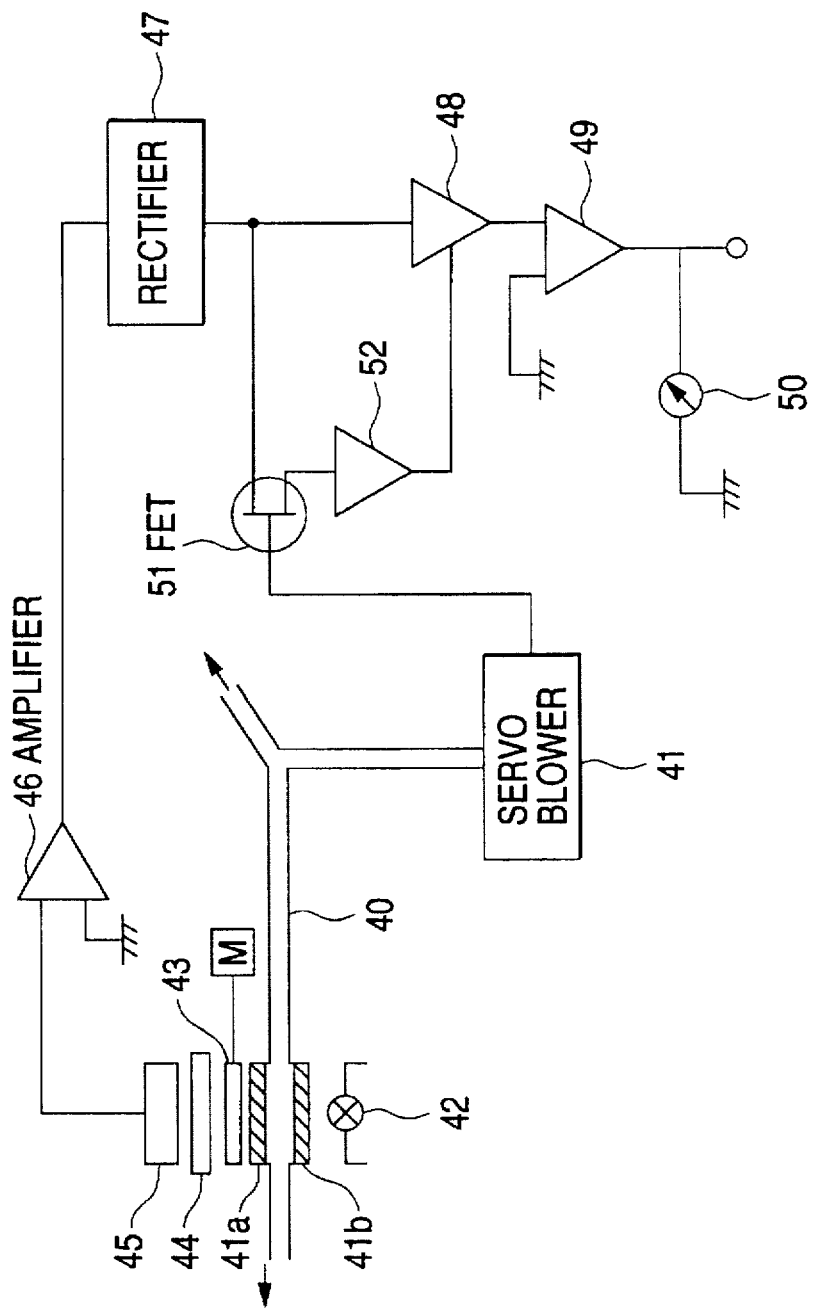
FIG. 9 shows diagrammatically the composition of a capnometer equipped with a conventional drift compensator.

Embodiments of the capnometer of the invention will now be described with reference to the accompanying drawings, in which FIG. 1 is a block diagram showing the composition of the capnometer of the invention; FIG. 2 is a flowchart describing the sequence of processing steps in the embodiment shown in FIG. 1; FIG. 3 illustrates the operating theory of the invention by showing points at which a maximum value is picked up from the detection signal of a thermal detector to perform drift compensation for determining a density signal from said detection signal; FIG. 4 illustrates how sensitivity correction is performed on the detection signal from the thermal detector; FIG. 5 is a timing chart for the case of turning off the radiation source at a specified period in the embodiment shown in FIG. 1; FIG. 6 is a timing chart for the case of turning off the radiation source in synchronism with inspiration; FIG. 7 is a timing chart for the case of turning off the radiation source when the difference between the maximum values picked up in adjacent inspiration phases exceeds a specified value in the embodiment shown in FIG. 1; and FIG. 8 is a timing chart showing the waveforms obtained by measuring the $CO_2$ concentration in the embodiment shown in FIG. 1.

Before going into details of the embodiments, we first describe the operating theory of the invention. The invention uses a thermopile as a thermal detector for sensing the intensity of an infrared radiation as it varies with the concentration of $CO_2$ in an expired gas. Thermopiles (e.g. Model S60 of Dexter Research Center, USA) are subject to a smaller amount of drift than the conventional PbSe and they are less expensive. On the other hand, thermopiles have unique properties and must be used in compliance with such characteristics. First of all, the light source chopping operation obtaining a response speeds slower than 25 ms are said to be necessary for accomplishing precise sampling with capnometers; however, thermopiles are so slow in response (50–200 ms) that it is difficult to meet this requirement for response.

Another problem with the capnometer using a thermopile is that the detection signal can potentially contain drift components due to various factors such as the change in the quantity of infrared rays from the radiation source, the clouding or contamination of the windows in the expired gas sensing portion and the structure of the thermopile per se. The drift component due to the structure of the thermopile must be compensated since it occurs on account of the change in the temperature of the environment in which the capnometer is used. Stated more specifically, the thermopile has many couples of hot and cold junctions and due to the time constant mismatch between the two junctions, a drift will appear in the detection signal. The hot junctions having a small heat capacity will respond rapidly to an abrupt change in the ambient temperature; however, the cold junctions which make thermal contact with the vessel or heat sink have a large heat capacity and do not respond as fast as the hot junction. As a result, the detection signal which is delivered in accordance with the temperature difference between the hot and cold junctions will contain an undesired drift component until the cold junction achieves thermal equilibrium with the ambient temperature.

The clouding or contamination of the windows in the expired gas sensing portion also reduces the transmission of infrared radiation, thereby changing the output of the thermopile, namely, an amplitude of the output. This affects the $CO_2$ concentration, making it impossible to perform consistent $CO_2$ measurements.

Therefore, the use of a thermopile in the measurement of $CO_2$ concentration requires that the detection signal from the thermopile be compensated for both the drift and the output variations.

In accordance with the invention, any drift that occurs in the detection signal from the thermopile due to its structure in response to an abrupt change in the ambient temperature is effectively compensated. The invention also enables the compensation for the change in the output sensitivity of the thermopile, corresponding to the amplitude, due to the clouding of the windows in the sensing portion or the variation in the quantity of an infrared radiation from the source.

A specific procedure for drift compensation comprises sensing a maximum value of the detection signal from the thermopile in each inspiration phase, storing the sensed maximum value, detecting an output value in each subsequent expiration phase and calculating the difference between the stored maximum value and the output value for the subsequent expiration phase so as to determine a density signal.

FIG. 3 illustrates how drift compensation is performed in a first embodiment of the invention. Symbols A, C and E refer to the points at which maxima in the detection signal from the thermopile were sensed during the inspiration phase, namely, for the inhaled gas substantially free from $CO_2$. Symbols B and D refer to the points at which signals were detected during expiration phases subsequent to points A and C, respectively, said signals having been reduced in accordance with the concentration of $CO_2$ in the exhaled gas. Consider, for example, point A. According to the invention, a maximum value Va is detected at point A during the inspiration phase and stored; then, an output value Vb is detected at point B during the subsequent expiration phase and subtracted from Va; this procedure is repeated for each cycle of inspiration and expiration phases. This embodiment, in which a maximum value for each inspiration phase is stored and held such that the difference from an output value for the subsequent expiration phase is determined, is effective in the case where the drift to be compensated is mild or small.

Besides, the maximum value in each inspiration phase is not limited by the maximum value of present inspiration phase. Namely, for example, when a value which corresponds to the maximum value is defined on a line connected between the adjacent maximum values of inspiration phase by a successive line or curve, the measurement value is not changed in a step manner in the case where if the drift to be compensated is large.

When performing the sensitivity correction in the present invention, the radiation source is turned off momentarily and then turned on. Stated more specifically, a maximum value is picked up from the detection signal of the thermopile during the inspiration phase immediately before the radiation source is turned off and the thus picked up maximum value is stored in the memory means. Then, a minimum value, such as the offset value, is picked from the detection signal of the thermopile when the radiation source is turned off. The difference between the stored maximum value and the minimum value is determined as a reference value corresponding to $CO_2$ concentration of zero and with a maximum reception of infrared radiation at that time and the thus determined reference value is stored in the memory means.

In addition, the ratio of the density signal as determined in the drift compensation mode to the stored reference value is calculated and this ratio is used to correct the sensitivity of the density signal. The correct $CO_2$ concentration can be computed on the basis of the compensation of the sensitivity of the density signal. Given the same $CO_2$ concentration, the ratio of the density signal to the reference signal remains the same even if the detection signal from the thermopile drops for a certain reason such as an abrupt change in the quantity of infrared radiation on account of the contamination of the windows in the sensing portion. Therefore, turning off the radiation source momentarily in the measurement of $CO_2$ concentration offers the advantage that even if the sensitivity of the output from the thermopile varies, the ratio of the density signal to the reference value may be calculated in the manner described above such that it is used to determine a density component which, in turn, is used to correct the $CO_2$ concentration, thereby ensuring the correct $CO_2$ measurement in a consistent manner.

The above-outlined operating theory of the invention will now be described by referring to the various values that are detected when compensating for the drift in the output of the thermopile and performing sensitivity correction on that output.

Normally, a maximum value Vc at point C in the present inspiration phase is detected and, in addition, an output value Vd at point D in the subsequent expiration phase is detected. The output value Vd is lower than Vc on account of $CO_2$ in the expired gas. The difference between Vc and Vd is calculated as a density signal Vx (=Vc–Vd). This procedure is repeated in successive inspiration and expiration phases and the density signal is calculated from the difference between each maximum value and the output value in the subsequent expiration phase, by so doing, effective drift compensation is accomplished even if the detection signal from the thermopile fluctuates due to an abrupt change in the ambient temperature.

In the next sensitivity correction mode, the radiation source is turned off momentarily and then turned on. A maximum (peak) value is detected at point A in the inspiration phase just before the radiation source is turned off and the detected peak value is stored in the memory means. When the radiation source is turned off, a minimum output value Vb is detected at point B and Vb is the offset voltage of the thermopile when the radiation is off. Subsequently, the difference between Va and Vb is determined as a reference value Vo (=Va–Vb) corresponding to $CO_2$ concentration of zero and with a maximum reception of infrared radiation at that time and the thus determined Vo is stored in the memory means.

At the same time, a maximum value Vc at point C in the present inspiration phase is detected and, in addition, an output value Vd at point D in the subsequent expiration phase is detected. The output value Vd is lower than Vc on account of $CO_2$ in the expired gas. The difference between Vc and Vd is calculated as a density signal Vx (=Vc–Vd).

Then, the ratio of Vx to Vo (=Vx/Vo) is determined and is used to calculate the correct $CO_2$ concentration through the Lambert-Beerslaw as follows:

$$Vx/Vo = 1 - e^{-\varepsilon c l}$$

where C: $CO_2$ concentration, e: absorbence coeffienct; and l: light path of infrared beam passing through respiratory gas (in FIG. 1, a distance between windows W1 and W2 of an air duct).

A similar method may be used to determine the corrected density component except in the case where the sensitivity of the thermopile output, serving as the amplitude, drops in response to the attenuation of infrared radiation due, for example, to the contamination or clouding of the windows due to $CO_2$ gas in the sensing portion. Referring again to FIG. 4, suppose that the output of the thermopile drops due to the attenuation of infrared radiation. In this case, a maximum value Ve is picked up from the detection signal of the thermopile at point E in the present inspiration phase and the thus picked up Ve is stored in the memory means. A minimum value Vf is then detected at point F and Vf is the offset voltage of the thermopile at the point of time when the radiation source is off. A reference value $V_{o1}$ corresponding to $CO_2$ concentration of zero and with a maximum reception of infrared radiation at that time is determined by subtracting Vf from Ve and stored in the memory means. A maximum value Vg is detected at point G in the subsequent inspiration phase; in addition, an output value Vh is detected at point H in the subsequent expiration phase. The output value Vh is lower than Vg on account of absorbance $CO_2$ in the expired gas. A density signal $V_{x1}$ is determined by subtracting Vh from Vg (Vg-Vh). Thereafter, the ratio of $V_{x1}$ to $V_{o1}$ ($=V_{x1}/V_{o1}$) is calculated and the correct $CO_2$ concentration is calculated on the basis of this ratio.

As just described above, the concept of the invention is also applicable to the case where the quantity of infrared radiation received by the thermopile drops for external reasons. Given the same $CO_2$ concentration, the ratio of the density signal to the reference value is constant ($Vx/Vo = V_{x1}/V_{o1}$); hence, the radiation source is turned off momentarily and then turned on to determine this ratio, which is used to perform sensitivity correction on the density signal which, in turn, is used to calculate the correct $CO_2$ concentration. Thus, by determining the ratio of the density signal to the reference value, one can determine the correct $CO_2$ concentration even if the sensitivity of the thermopile output varies on account of the attenuation of the infrared radiation being received by the thermopile.

Referring now to FIG. 1, symbol T designates an air way adapter through which both the expired and inspired gas will pass. Windows W1 and W2 each made of a transparent material such as a plastic sheet are formed in opposed areas of the air way adapter. One end portion of air duct T (which is on the left of FIG. 1) serves as a mouthpiece which is to be inserted into the mouth of the patient and the other end portion (which is on the right of FIG. 1) is open to the atmosphere. Both windows W1 and W2 are protected against clouding such as with the water vapor in the expired gas. An infrared radiation source 1 such as an ir lamp is provided just above the window W1 such that an infrared radiation is applied through the window W1. A thermal detector 2 in the form of the above-described thermopile is provided just below the window W2 such that the infrared radiation supplied from the source 1 through the windows W1 and W2 is detected. A filter F is located above the light-sensing area of the thermal detector 2 and it selectively passes those rays which have such a wavelength (ca. 4.3 μm) that they are absorbed by carbon dioxide in the expired gas.

Shown by 3 is a radiation source drive unit that is typically composed of a constant-current circuit and which is turned on and off by means of a switch SW. Switch SW is typically composed of an electronic switch such as a transistor and turned on and off in response to a control signal supplied from a control unit 6 to be described later.

Shown by 4 is an amplifier for amplifying the detection voltage from the thermal detector 2; 5 is an analog-digital converter for converting the output of the amplifier 4 to a digital signal. Control unit 6 is typically composed of a CPU and controls the overall system in accordance with a $CO_2$ measuring control program stored in ROM 9 which will be described later.

Shown by 7 is a manipulating section typically composed of a plurality of buttons which are to be touched for setting various parameters such as the period at which the radiation source 1 is to be turned off momentarily and then turned on and the upper limit for the detection signal from the thermal detector 2, as well as providing settings of the necessary data.

Shown by 8 is a RAM that temporarily stores and holds the parameter settings, as well as the maxima picked up from the detection signal of the thermal detector 2, the calculated reference value, the measured $CO_2$ concentration and other data. Shown by 9 is a ROM which contains a control program for performing automatic $CO_2$ concentration measurements by drift and sensitivity compensation on the detection signal from the thermal detector 2 in accordance with the above-described operating theory of the present invention.

Shown by 10 is an indicator typically composed of a plurality of light-emitting devices such as LEDs or an audible device such as a buzzer. The light-emitting devices present varying $CO_2$ concentrations in a bar graph; alternatively, the buzzer signals $CO_2$ concentration changes by a modulated sound. If desired, LEDs may be combined with a buzzer to monitor the breathing of the patient in both a visible and audible manner.

The operation of the capnometer having this structure will now be described with reference to the flowchart shown in FIG. 2. At the commencement of measurement, the power switch (not shown) is thrown to turn on the radiation source 1 (step S1). Thereafter, the patient is allowed to breathe so that his respiratory gas goes into and comes out of the air way adapter T via the mouthpiece inserted into his mouth. The transmission of the radiation which varies with the change in the $CO_2$ concentration of the respiratory gas is received by the thermal detector 2 in such a way that the point at which the detector 2 delivers an increased output is recognized as an inspiration and a maximum value is picked up from the detection signal of the thermal detector 2 during the present inspiration phase and stored in RAM 8 (step S2). The desired maximum value can be identified by performing a suitable processing on the detection signal from the thermal detector 2, for example, by calculating the differential for successive data.

Then, a lower detection signal delivered from the thermal detector 2 at a time subsequent to the detection of the present maximum value is recognized as representing an expiration and the value of the detection signal from the thermal detector 2 that decreased on account of the $CO_2$ in the expired gas is picked up and compared with the stored maximum value for the inspiration phase. The difference between the two values is calculated to determine a density signal (step S3).

Then, the radiation source 1 is turned off momentarily (step S4). The resulting minimum value of the detection signal from the thermal detector 2 is compared with the stored maximum value and the difference is determined and stored as a reference value corresponding to $CO_2$ concentration of zero and with a maximum reception of the infrared radiation at that time (step S5).

The density signal calculated in step S3 is divided by the reference value corresponding to $CO_2$ concentration of zero and the density signal is amplitude corrected by the resulting ratio to calculate the correct density component (step S6). On the basis of this density component, the $CO_2$ concentration is determined and sent to the indicator 10, which presents it in a bar graph consisting of bars that vary in length in accordance with the $CO_2$ concentration profile shown in FIG. 8 (step S7).

Thus, in the embodiment just described above, the thermal detector 2 comprising a thermopile is used and a maximum value is picked up from the detection signal of said thermal detector during successive inspiration phases and the difference from an output value obtained during the expiration phase subsequent to each inspiration phase is determined to perform drift compensation; in addition, the radiation source 1 is turned off momentarily such as to perform sensitivity correction on the output of the thermal detector for calculating the $CO_2$ concentration. In this way, the capnometer of the invention enables consistent $CO_2$ concentration measurement.

The flowchart shown FIG. 2 assumes that the radiation source 1 is turned off at a period of unspecified intervals. If desired, the period T at which the radiation source 1 is turned off may be predetermined as shown in FIG. 5. The period T may be preset and stored in ROM 9 or it may be set manually via the manipulating section 7. In either way, predetermining the period of turning off the radiation source 1 enables automatic correction of the detection signal from the thermal detector 2. The period may be set at any desired value such as 30 seconds or 1 minute depending on the ambient temperature.

Alternatively, the radiation source 1 may be turned off at a period associated with the inspiration, such as in synchronism with two or more inspirations or when one breathing cycle (consisting of one inspiration and one expiration) ends. The number of inspirations may be preset and stored in ROM 9 or it may be set manually via the manipulating section 7. If the radiation source 1 is turned off at a specified period as shown in FIG. 5, its turning off may sometimes coincide with the expiration phase and the data detected on this occasion is not useful. On the other hand, if the radiation source 1 is turned off in synchronism with the inspiration, the detection signal delivered during expiration phases can be corrected positively to insure consistency in $CO_2$ measurement.

Another approach that can be taken is illustrated in FIG. 7; a specified value is set for the drift of the detection signal from the thermal detector 2 and the radiation source is turned off momentarily when the drift exceeds this specified value. For instance, two maximum values are picked up, one in the present inspiration phase and the other in the preceding inspiration phase, and if the difference between these values exceeds 4 mmHg which is corresponding to the pertial pressure of $CO_2$, the radiation source 1 may be turned off. In the case shown in FIG. 7, the radiation source 1 is turned off when the difference between maximum values P1 and P2 exceeds the specified value and when the difference between P3 and P4 exceeds the same specified value. As in the case described with reference to FIG. 5, the specified value may be set manually via the manipulating section 7 or, alternatively, it may be preliminarily stored in ROM 9 such that the control unit 6 monitors it to control the turning off of the radiation source 1. The provision of such specified value for the drift of the detection signal from the thermal detector 2 ensures that the measurement of $CO_2$ concentration can be accomplished both positively and consistently even in environments where the ambient temperature varies greatly.

Advantages of the Invention:

As will be understood from the foregoing description, the capnometer of the invention which is recited in claim 1 is characterized by the use of a thermal detector comprising a thermopile and this eliminates the need to employ mechanical parts, such as a chopper (radiation interrupter) and a motor for driving it to rotate, that have been necessary in the conventional radiation detectors. This offers the advantage of providing ease in reducing the overall size of the system while increasing its ruggedness and reducing the production cost. The capnometer of claim 1 is also adapted for sensitivity correction by turning the radiation source off and on at unspecified intervals.

In the embodiment recited in claim 2, the drift of the detection output due to an abrupt change in the ambient temperature or the variation in the output sensitivity due to the clouding or contamination of the windows in the sensing portion can be automatically corrected by turning the radiation source off and on at specified periods and this offers the advantage of enabling correct $CO_2$ concentration measurements in a consistent manner.

In the embodiment shown in claim 3, the radiation source is turned off in synchronism with the inspiration and this offers the advantage of achieving positive correction of the detection signal for expiration phases even if the sensitivity of the thermal detector changes on account of variations in the ambient temperature and the clouding or contamination of the windows in the air way adapter.

In the embodiment shown in claim 4, the radiation source is turned off when the output of the thermal detector exceeds a predetermined value and this offers the advantage of enabling the $CO_2$ concentration of respiratory gases to be measured consistently even in environments where the ambient temperature experiences great variations.

What is claimed is:

1. A capnometer comprising:
 a light source for irradiating an infrared radiation to respiratory gas;
 a thermal detector for sensing the transmission of said infrared radiation;
 means for turning said light source on and off at predetermined intervals;
 a memory for storing output from said thermal detector; and
 control means for picking up a maximum value of said detection signal from said thermal detector for the present inspiration phase, for storing said maximum value in said memory and calculating the difference between a subsequently issued detection signal and said maximum value, for compensating a drift resulting from the characteristics of said thermal detector to determine a density signal, for picking up a minimum output value, corresponding to an offset value, of said detection signal from said thermal detector when said light source is turned off momentarily, for calculating the difference between said minimum value and said maximum value for the present inspiration phase, for storing the difference in said memory as a reference value corresponding to carbon dioxide concentration of zero and with a maximum reception of infrared radiation at that time, for storing said reference value in said memory, for calculating the ratio of said density signal to said reference value, and for determining the concentration of carbon dioxide by correcting said density signal in accordance with said ratio.

2. A capnometer according to claim 1, wherein said means for turning said light source on and off turns off said light source at a specified cycle longer than the cycle of respiration.

3. A capnometer according to claim 1, wherein said means for turning said light source on and off turns off said light source in synchronism with inspiration.

4. A capnometer according to claim 1, wherein said means for turning said light source on and off turns off said light source when the difference between maximum values detected in adjacent inspiration phases exceeds a predetermined value.

5. A capnometer according to claim 2, wherein said means for turning said light source on and off turns off said light source when the difference between maximum values detected in adjacent inspiration phases exceeds a predetermined value.

6. A capnometer according to claim 3, wherein said means for turning said light source on and off turns off said light source when the difference between maximum values detected in adjacent inspiration phases exceeds a predetermined value.

7. A method for measuring the concentration of carbon dioxide in respiratory gas, comprising the steps of:

irradiating an infrared radiation from a light source to said respiratory gas;

sensing the transmission of said infrared radiation;

turning said light source on and off at predetermined intervals;

detecting radiation transmitted through said respiratory gas with a thermal detector:

storing output from said thermal detector;

detecting a maximum value of a detection signal output from said thermal detector for the present inspiration phase;

storing said maximum value in a memory;

calculating the difference between a subsequently issued detection signal and said maximum value;

compensating a drift resulting due to the characteristics of said thermal detector to determine a density signal;

detecting a minimum output value, corresponding to an offset value, of said detection signal from said thermal detector when said light source is turned off momentarily;

calculating the difference between said minimum value and said maximum value for the present inspiration phase;

storing a value representing the difference in said memory as a reference value corresponding to carbon dioxide concentration of zero and with a maximum reception of infrared radiation at that time;

storing said reference value in said memory.

calculating the ratio of said density signal to said reference value; and determining the concentration of carbon dioxide in said respiratory gas by correcting said density signal in accordance with said ratio.

8. A method for measuring the concentration of carbon dioxide in said respiratory gas according to claim 7, further comprising the step of turning said light source off at a specified cycle longer than the cycle of respiration.

9. A method for measuring the concentration of carbon dioxide in said respiratory gas according to claim 7, further comprising the step of turning said light source off in synchronism with the inspiration.

10. A method for measuring the concentration of carbon dioxide in said respiratory gas according to claim 7, further comprising the step of turning the light source off when the difference between maximum values detected in adjacent inspiration phases exceeds a predetermined value.

11. A method for measuring the concentration of carbon dioxide in said respiratory gas according to claim 8, wherein said step of turning of said light source comprises the step of turning the light source off when the difference between maximum values detected in adjacent inspiration phases exceeds a predetermined value.

12. A method for measuring the concentration of carbon dioxide in said respiratory gas according to claim 9, wherein said step of turning said light source off comprises the step of turning the light source off when the difference between maximum values detected in adjacent inspiration phases exceeds a predetermined value.

* * * * *